United States Patent [19]
Collier

[11] Patent Number: 5,800,570
[45] Date of Patent: Sep. 1, 1998

[54] LOWER EXTREMITY PROSTHETIC DEVICE

[76] Inventor: Milo S. Collier, 1152 Douglas St., Longview, Wash. 98632

[21] Appl. No.: 618,450

[22] Filed: Mar. 14, 1996

[51] Int. Cl.⁶ .................................................. A61F 2/66
[52] U.S. Cl. ................................................ 623/55; 623/53
[58] Field of Search ............................. 623/55, 56, 54, 623/53, 47, 50, 52

[56] References Cited

U.S. PATENT DOCUMENTS

| | | |
|---|---|---|
| 598,230 | 2/1898 | Roberts et al. |
| 1,294,632 | 2/1919 | Dickson ........................... 623/55 X |
| 1,804,915 | 5/1931 | Collins . |
| 2,036,830 | 4/1936 | Rowley . |
| 2,197,093 | 4/1940 | Campbell . |
| 2,472,819 | 4/1949 | Giesen . |
| 2,475,372 | 7/1949 | Catranis . |
| 3,874,004 | 4/1975 | May . |
| 4,328,594 | 5/1982 | Campbell et al. . |
| 4,547,913 | 10/1985 | Phillips . |
| 4,636,220 | 1/1987 | Ziegelmeyer . |
| 4,645,509 | 2/1987 | Poggi et al. . |
| 4,721,510 | 1/1988 | Cooper et al. . |
| 4,822,363 | 4/1989 | Phillips . |
| 4,938,776 | 7/1990 | Masinter . |
| 4,959,073 | 9/1990 | Merlette . |
| 5,116,381 | 5/1992 | Palfray ............................ 623/33 |
| 5,116,384 | 5/1992 | Wilson et al. . |
| 5,181,933 | 1/1993 | Phillips ............................ 623/55 |
| 5,314,499 | 5/1994 | Collier ............................. 623/47 |
| 5,443,528 | 8/1995 | Allen ............................... 623/52 |

FOREIGN PATENT DOCUMENTS 2092451   8/1982   United Kingdom .

*Primary Examiner*—David H. Willse
*Attorney, Agent, or Firm*—Kolisch, Hartwell, Dickinson, McCormack & Heuser

[57] ABSTRACT

The present invention is a lower extremity prosthetic device which includes a modular foot having a heel member and an elongate, dorsal midfoot member configured for detachable combination via a coupling mechanism. The heel member is formed substantially from a first structural material of a first modulus of elasticity. The midfoot member is formed substantially from a second structural material having a second modulus of elasticity less than the first modulus of elasticity. The midfoot member extends arcuately forwardly from the heel member, and is configured with differentially flexible lateral and medial elements which provide the device with flexion characteristics similar to those of a natural foot. An elongate plantar member extends between the heel member and a forward end of the midfoot member, the plantar member being formed substantially from a third material having a third modulus of elasticity which is lower than the second modulus of elasticity. The plantar member includes a toe section and a sub-arch section. The sub-arch section extends arcuately between the heel member and the forward end of the midfoot member. The toe section extends forwardly from the sub-arch section.

14 Claims, 3 Drawing Sheets

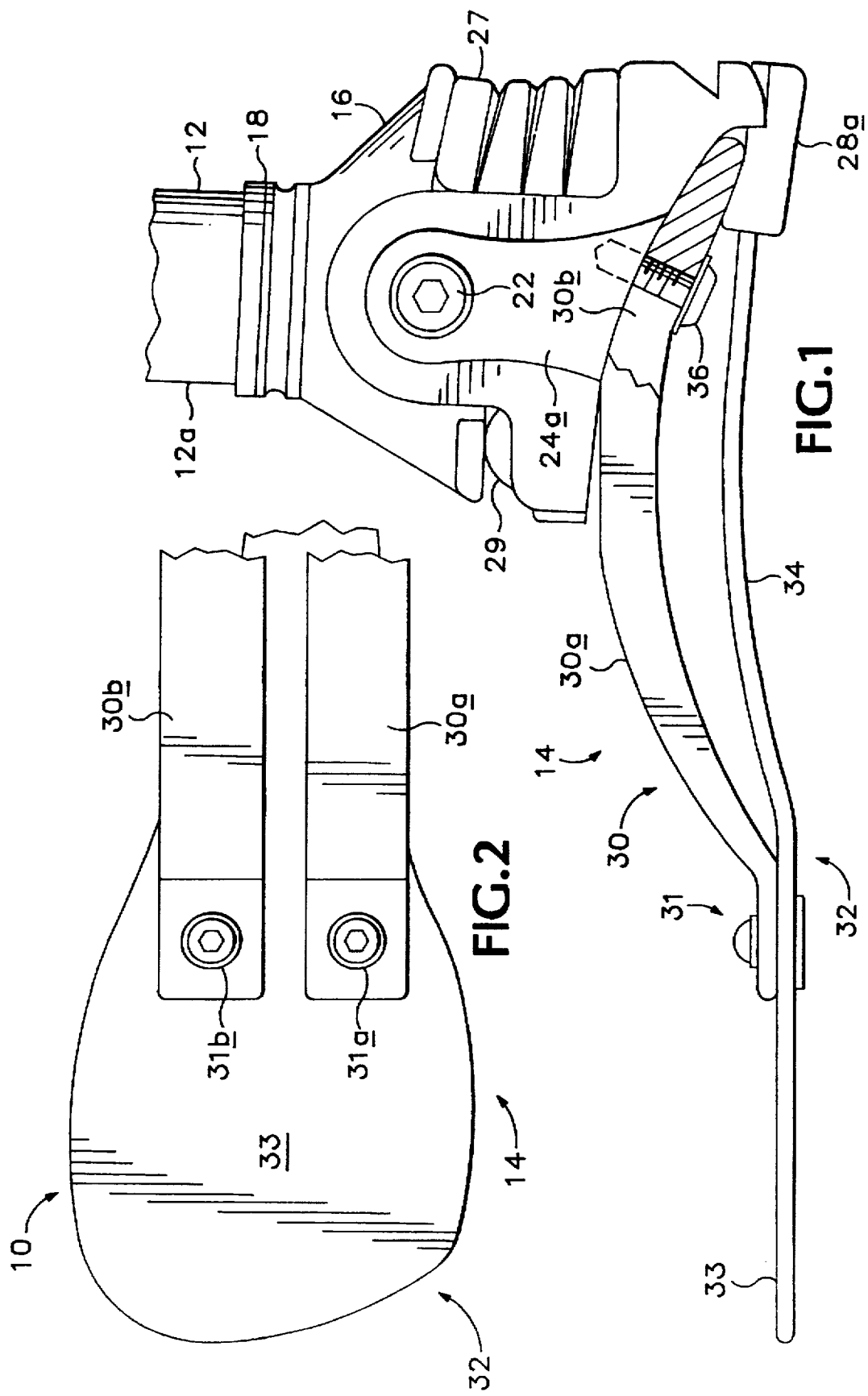

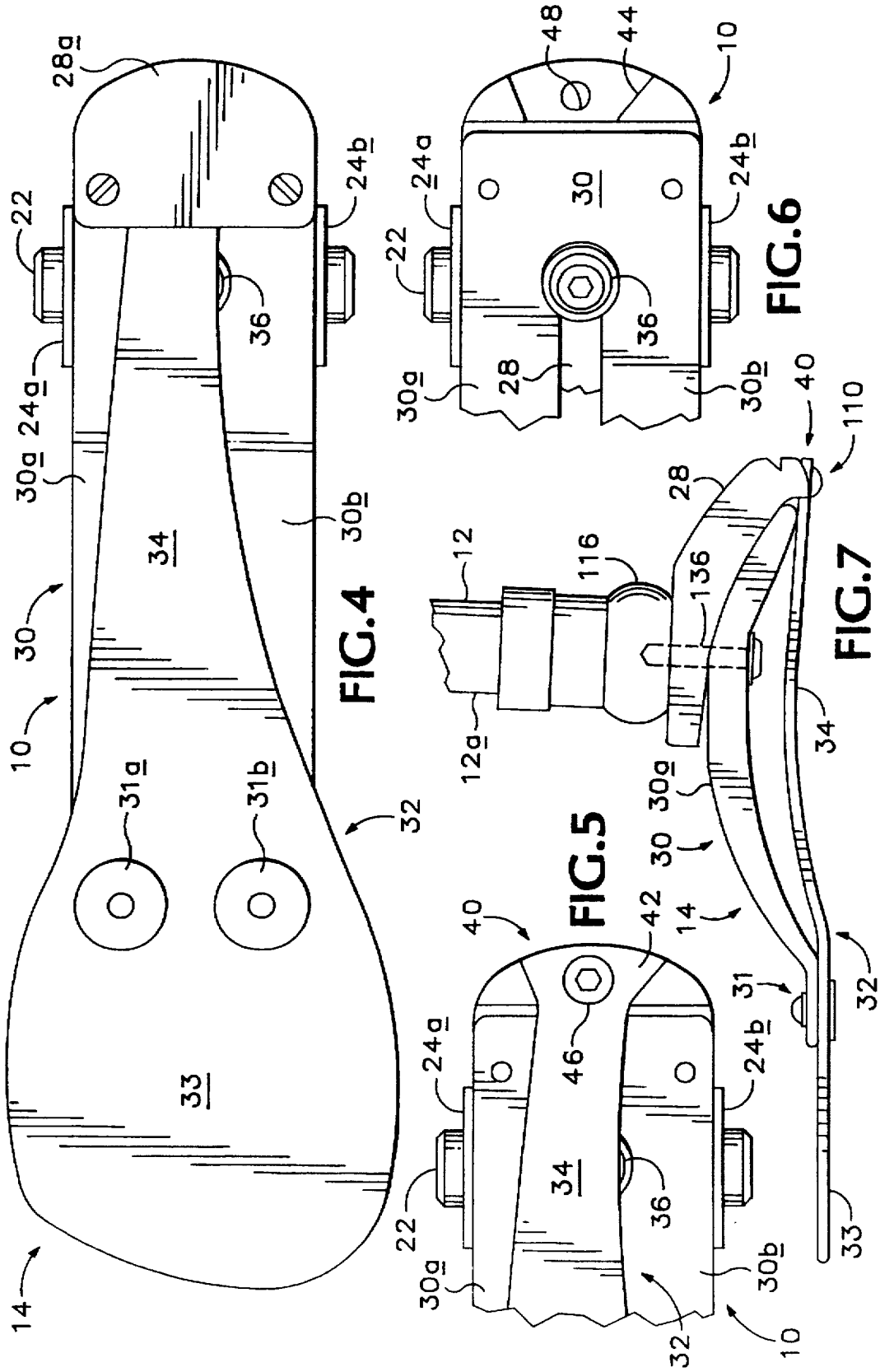

LOWER EXTREMITY PROSTHETIC DEVICE

TECHNICAL FIELD

This invention relates generally to prosthetic devices and, more particularly, to a prosthesis for use by lower extremity amputees. The invented prosthesis includes an artificial foot, and further may include an artificial ankle and shin. A modular design is used, allowing for user-specific prosthesis construction, accommodating the repair of individual components, and giving the prosthesis characteristics which are more similar to the characteristics of a natural limb.

BACKGROUND ART

A prosthetic device, or simply a prosthesis, is an artificial substitute for a part of the body such as a limb. Numerous prostheses have been developed to serve this purpose, each trying to replicate the function and appearance of the missing body part.

Lower leg prosthetic devices present unique problems. They must be strong enough to support the weight of a person and to withstand the forces encountered when walking or running, but they also must be light enough to allow comfortable use. This dichotomy is complicated further by the increasing number of lower-limb amputees who desire to participate in athletic activities. For such activities, amputees require prosthetic devices which have mobility very similar to their original limb. Lower leg/foot prosthetic devices must be similar enough in mobility to natural legs/feet to accommodate athletic activity while remaining both strong and comfortable to the user.

DISCLOSURE OF THE INVENTION

The present invention provides a lower extremity prosthetic device which includes a modular foot structure having a heel member and an elongate, dorsal midfoot member configured for detachable combination via a coupling mechanism. The heel member is formed substantially from a first structural material of a first predetermined modulus of elasticity to define a stable support structure. The midfoot member is secured to the heel member and extends forwardly therefrom in an arc so as to provide the foot structure with flexion characteristics similar to those of a natural foot. The midfoot member typically is formed from a second structural material having a second predetermined modulus of elasticity which is less than the first modulus of elasticity, thereby providing for differentiated longitudinal flexion of the foot structure under stride-related forces. Such forces are those which occur due to walking, jogging, running or jumping while wearing a prosthesis.

In accordance with one aspect of this invention, the midfoot member has a pair of adjacent medial and lateral arch elements, each extending arcuately from the heel member to an area corresponding to the metatarsus of a natural foot (i.e., the metatarsal region of the foot structure). The arch elements typically are spaced, thereby accommodating torsional flexion of the foot structure upon the application of a stride-related force. Thus, the foot structure is configured for flexure which is similar to the flexure of a natural foot.

In accordance with another aspect of the invention, the foot structure includes an elongate plantar member joined to the heel member and extending forwardly therefrom. The plantar member is formed substantially from a third structural material having a third predetermined modulus of elasticity which provides for further differentiated longitudinal flexion of the foot. The third modulus of elasticity typically is less than both the first and second modulus of elasticity. In the preferred embodiment, the plantar member has a sub-arch section which extends arcuately forwardly from the heel member to the metatarsal region of the foot structure, and a toe section which extends forwardly from the sub-arch section. The plantar member flexes longitudinally in response to stride-related forces.

These and other objects and advantages of the present invention will be more readily understood after a consideration of the drawings and the detailed description of the preferred embodiment which follows.

BRIEF DESCRIPTION OF THE DRAWINGS

FIG. 1 is a partially sectioned, side elevational view of a prosthesis constructed in accordance with a preferred embodiment of the invention, such prosthesis including a heel member, an arcuate midfoot member, and a plantar member which extends between the heel and metatarsal regions of the foot.

FIG. 2 is a fragmentary top plan view of the prosthesis depicted in FIG. 1.

FIG. 4 is a bottom view of the prosthesis depicted in FIG. 1.

FIG. 5 is a fragmentary bottom view of the prosthesis depicted in FIG. 1, but with a heel cushion removed to reveal a connection between the heel and plantar members of the prosthesis.

FIG. 6 is a fragmentary bottom view of the prosthesis depicted in FIG. 1, but with both the heel cushion and plantar member removed to reveal a connection between the heel and midfoot members.

FIG. 7 is a side elevational view of an alternative embodiment prosthesis constructed in accordance with the invention.

Figure 3:
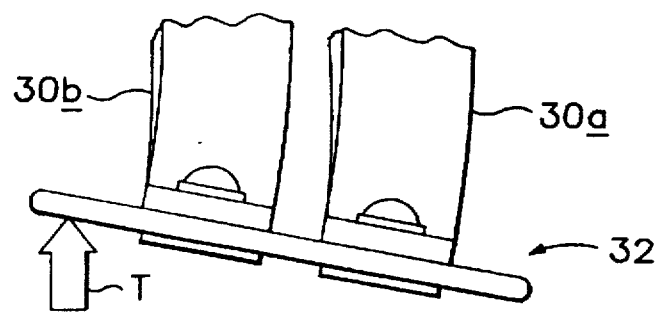
FIG. 3 is a somewhat simplified, fragmentary front elevational view of the prosthesis shown in FIG. 1, such view illustrating torsional flexion of the midfoot member.

DETAILED DESCRIPTION OF THE PREFERRED EMBODIMENT AND BEST MODE FOR CARRYING OUT THE INVENTION

A preferred embodiment of the invented prosthetic device is shown in FIGS. 1–6, the device being indicated generally at 10. As indicated, the prosthetic device readily is divided into three structures, an artificial shin structure 12, an artificial foot structure 14, and an artificial ankle structure 16. In some instances, the device further includes an artificial knee structure (not shown), allowing for use by above-the-knee amputees. Further, it will be appreciated that the prosthetic device commonly will be covered by artificial skin (not shown) made from a material such as rubber so as to simulate skin.

Referring initially to shin structure 12, it will be noted that such shin is an elongate member, including a first end 12a which connects to the ankle or foot, and a second end (not shown) which connects to an amputation socket or knee. The first end of the shin is secured to a mount 18, the mount defining a bore which is sized and shaped to receive a generally vertical bolt which forms a part of the shin. In the depicted embodiment, mount 18 is integrally formed with ankle 16.

Ankle 16 includes a pin 22 which extends between a pair of support arms 24a, 24b which typically are formed integrally with the foot. The support arms extend upwardly from opposite sides of the foot to capture a downwardly extending portion of ankle 16. The pin extends through holes in the support arms and is readily removable so as to accommodate separation of the ankle and foot during repairs. A first resilient element 27 is mounted intermediate the foot and ankle, the first resilient element tending to urge the ankle to pivot counterclockwise to its position in FIG. 1. The pivot force exerted by the first resilient element, however, is opposed by a second resilient element 29, which acts oppositely on the ankle to allow pivot of the ankle either forward or backward from the metatarsal position shown in FIG. 1. Both the first and second resilient elements may be formed from a material such as foam rubber, providing yieldable resistance to pivot of the ankle about the pin.

The ankle and shin preferably are constructed in a manner similar to that set forth in U.S. patent application Ser. No. 08/332,655, filed Nov. 1, 1994. The disclosure of which is incorporated herein by this reference. Alternatively, the ankle and shin may be constructed in a manner set forth in U.S. Pat. No. 5,314,499, filed on Apr. 4, 1991, and issued on May 24, 1994. The disclosure of the patent also is incorporated herein.

Referring now to foot structure 14, it will be noted that the depicted foot is of a modular construction, including a heel member 28, a midfoot member 30 and a plantar member 32. Such members are removably coupled with one another, allowing for easy disassembly and repair. Further, because the foot is modular, it will be appreciated that it is possible to construct a foot which has user-specific flexion characteristics, such characteristics being dependent on the shape of the individual members and on the materials used.

Heel member 28 typically is formed from a material such as glass-reinforced nylon or carbon graphite composite, and is constructed to at least partially define an arch. Heel member 28 is hidden in FIGS. 1–6, but is shown in FIGS. 7–8B. As should be apparent, the heel member generally defines a heel region of the foot. The heel region typically is fitted with a heel cushion 28a which lessens heel impact.

As shown in FIG. 1, midfoot member 30 is arch-shaped. It is configured to extend forwardly from the heel member to a metatarsal region of the foot. The midfoot member thus extends from the foot's heel region to that portion of the foot which corresponds to the ball of a natural foot. In the preferred embodiment, midfoot member 30 has a pair of elongate arch elements: a lateral arch element 30a on the lateral side of the foot; and a medial arch element 30b on the medial side of the foot. The arch elements are generally parallel, and are transversely spaced to provide for differential torsional flexion of said foot structure upon application of stride-related force. This gives the foot structure a response characteristic more similar to that of a natural foot. FIG. 3 illustrates the torsional flexion of the arch elements upon the application of a force, indicated by force arrow T. Midfoot member 30 is attached to plantar member 32 in the metatarsal region of the foot. In particular, lateral arch element 30a is attached to the plantar member via a fastener 31a. Likewise, medial arch element 30b is attached to the plantar member via a fastener 31b.

In accordance with my teachings, heel member 28 is formed substantially from a first structural material having a first modulus of elasticity. The midfoot member is formed substantially from a second structural material having a second modulus of elasticity which is less than the first modulus of elasticity. The flexibility of the materials (and the arched shape of the heel-midfoot combination) is selected to allow the foot structure to act as an energy storage spring which absorbs energy on impact. The different moduluses of elasticity of the heel and midfoot members provide for a differentiated longitudinal flexion of the foot upon the application of a stride-related force. In particular, such differential longitudinal flexion will occur due to activities such as walking, jogging, running, jumping or other activities which would cause a natural foot to flex.

Turning now to a discussion of plantar member 32, it will be noted that the plantar member extends arcuately forwardly from the heel member to the midfoot member and it is secured to the midfoot member in an area which corresponds to the ball of a natural foot. As indicated, plantar member 32 includes a toe section 33 and a sub-arch section 34. The toe section is sized and shaped to emulate a natural forefoot (toe region). Sub-arch section 34 is sized and shaped to emulate the lateral tendons and ligaments of a natural foot. The sub-arch section thus extends forwardly from the heel member in a lesser arc than the midfoot member. The toe section is joined with the sub-arch section in the metatarsal region of the foot. The toe and sub-arch sections preferably are integrally formed. Like the midfoot member, the sub-arch section of the plantar member longitudinally flexes in response to application of a stride-related force. Also, the sub-arch section is laterally offset from a longitudinal center line of the foot structure, thereby providing additional support on the lateral side of the foot structure.

As shown in FIGS. 5 and 6, plantar member 32 connects to heel member 28 using a tongue-and-groove fastening arrangement 40. The fastening arrangement includes a flared tongue 42, which forms a part of the sub-arch section, and a V-shaped groove 44, which is defined in the heel member. The groove is configured to receive and hold the tongue, resisting both longitudinal and side-to-side movement of the tongue. The connection of the tongue in the groove also is secured elevationally in place by a fastener 46 which extends through the tongue and into bore 48, which is defined in the heel member.

In the preferred embodiment, the plantar member is formed substantially from a third structural material having a third modulus of elasticity which is less than the first and second moduluses of elasticity. This differential elasticity provides for further differentiated longitudinal flexion of the foot upon the application of stride-related force.

An alternative embodiment of the invented prosthetic device is shown in FIG. 7, the alternative embodiment device being indicated generally at 110. As should be apparent, prosthesis 110 is a simplified version of prosthesis 10. The alternative embodiment prosthesis has a rigid ankle structure 116. Such ankle structure is attached to the foot via a coupling mechanism employing a generally vertical pin 136. The present invention is fully embodied by prosthesis 110.

Figure 8A:
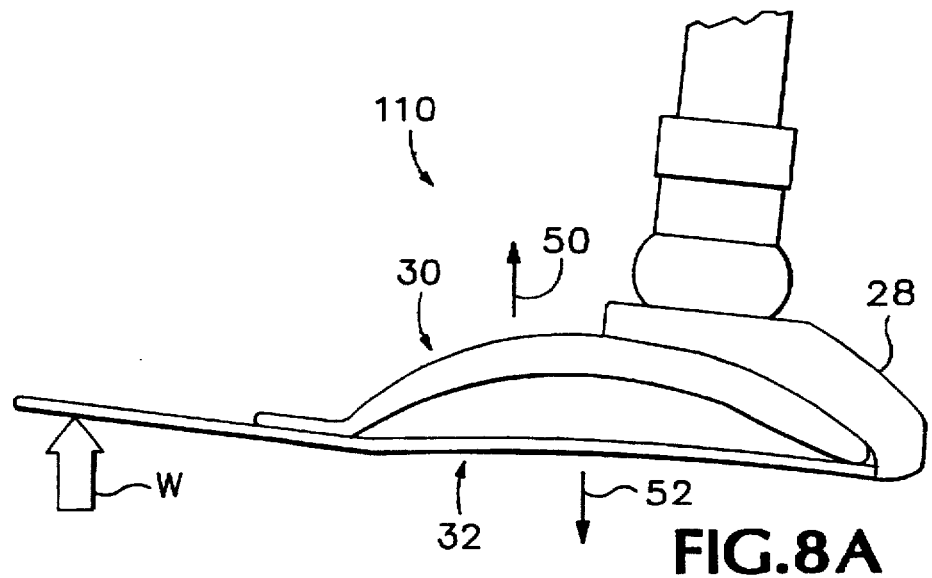
FIG. 8A is a side elevational view of the prosthesis of FIG. 7, such view illustrating counter-flexion of the midfoot and plantar members when a first stride-related force is applied to the foot.
Figure 8B:
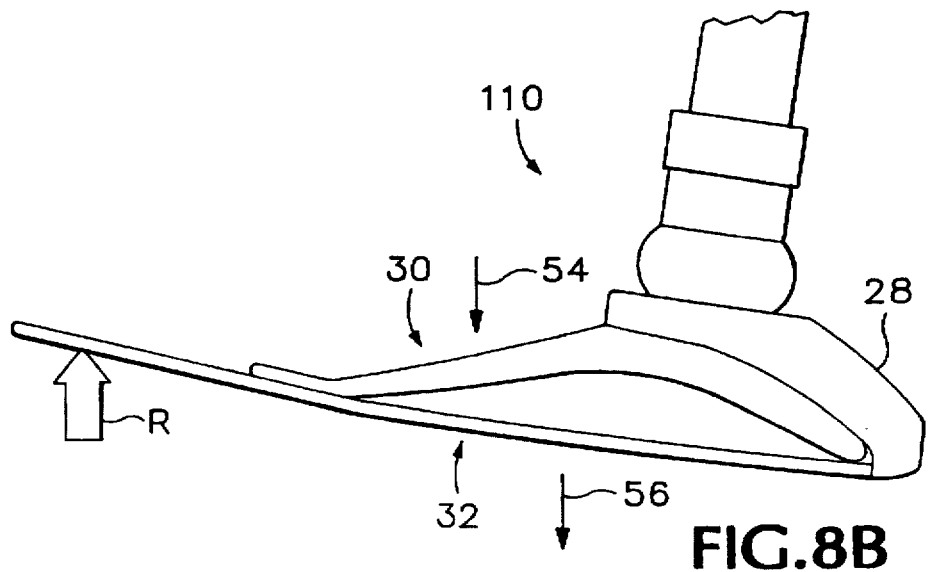
FIG. 8B is side elevational view of the prosthesis of FIG. 7, such view illustrating mutual flexion of the midfoot and plantar members when a second stride-related force is applied to the foot.

As illustrated in FIGS. 8A and 8B, plantar member 32 and midfoot member 30 flex in response to stride-related forces, collectively exhibiting at least two load-responsive phases of longitudinal flexion. These phases are determined by the extent of stride-related force applied to the foot structure. In FIG. 8A, for example, a first phase (or walking phase) is shown. Such phase corresponds to a first amount of force (as indicated by force arrow W) being applied to the foot. Upon application of this force, the midfoot and plantar members exhibit counter-flexion, wherein the midfoot and plantar members flex in opposite directions (as indicated by arrows 50 and 52). In FIG. 8B, the second phase (or running phase) is shown. The second phase corresponds to a second amount of force (as indicated by force arrow R) being applied to the foot where the second amount of force is greater than the first amount of force (i.e., R>W). Upon application of the second amount of force, the midfoot and plantar members exhibit mutual flexion, wherein the midfoot and plantar members flex together in a common direction (as indicated by arrows 54 and 56).

It will be appreciated that combination of the heel member and midfoot member is achieved via a coupling mechanism, such as pin 36 (or pin 136 in FIG. 7) or some other coupling arrangement as disclosed in the above-referenced, incorporated patent application. Pin 36 (or alternatively 136) typically extends into the heel member and fits between the lateral and medial arch elements 30a, 30b.

While the preferred embodiments and best mode of the invention have been disclosed, those skilled will understand that variations and changes may be made without departing from the spirit and scope of the invention as defined by the claims.

I claim:

1. A lower extremity prosthetic device which includes a foot structure, the foot structure comprising:

a heel member;

an elongate, dorsal midfoot member joined to said heel member and extending forwardly therefrom in an arc, said midfoot member including elongate medial and lateral arch elements, said arch elements being transversely spaced to accommodate torsional flexion of said foot structure upon application of a stride-related force; and an elongate plantar member which extends between said heel member and a forward end of said midfoot member, said plantar member being configured to longitudinally flex in response to application of a stride-related force to said foot structure.

2. The prosthetic device of claim 1, wherein said heel member is formed from a first structural material having a first predetermined modulus of elasticity, said midfoot member is formed substantially from a second structural material having a second predetermined modulus of elasticity less than said first modulus of elasticity, and said plantar member is formed substantially from a third structural material having a third predetermined modulus of elasticity less than said second modulus of elasticity, thereby providing for differentiated longitudinal flexion of said foot structure upon application of stride-related force.

3. The prosthetic device of claim 1, wherein said plantar member includes a toe section and an elongate sub-arch section, said sub-arch section extending arcuately between said heel member and a forward end of said midfoot member, said toe section extending forwardly from said forward end of said midfoot member.

4. The prosthetic device of claim 3, wherein said sub-arch section of said plantar member is positioned below said midfoot member, said sub-arch section and said midfoot member being configured to flex in response to application of a stride-related force, and to collectively exhibit at least two load-responsive phases of longitudinal flexion, said load-responsive phases including:

a first phase wherein a first force is applied to said foot structure, said midfoot member and said sub-arch section exhibiting counter-flexion wherein said midfoot member and said sub-arch section flex in opposite directions; and a second phase wherein a second force is applied to said foot structure, said second force being greater than said first force, said midfoot member and said sub-arch section exhibiting mutual flexion wherein said midfoot member and said sub-arch section flex together.

5. A lower extremity prosthetic device including a foot structure which comprises:

a heel member formed substantially from a first structural material of a first modulus of elasticity;

an elongate, dorsal midfoot member joined to said heel member and extending forwardly therefrom in an arc, said midfoot member being formed substantially from a second structural material having a second modulus of elasticity less than said first modulus of elasticity; and an elongate plantar member bridging a distance between said heel member and a forward end of said midfoot member, said plantar member being formed substantially from a third structural material having a third modulus of elasticity less than said second modulus of elasticity.

6. The prosthetic device of claim 5, wherein said plantar member includes a toe section and a sub-arch section, said sub-arch section extending arcuately between said heel member and said forward end of said midfoot member, and said toe section extending forwardly from said sub-arch section, said plantar member being configured to flex longitudinally in response to application of a stride-related force to said foot structure.

7. The prosthetic device of claim 6, wherein said foot structure further comprises a tongue-and-groove fastening arrangement for fastening said sub-arch section of said plantar member to said heel member, said fastening arrangement including a flared tongue which forms a part of said plantar member and a correspondingly-shaped groove defined in said heel member, wherein said groove is configured to receive and hold said tongue.

8. The prosthetic device of claim 6, wherein said sub-arch section is laterally offset from a longitudinal center line of said foot structure.

9. The prosthetic device of claim 6, wherein said sub-arch section of said plantar member is positioned below said midfoot member, said sub-arch section and said midfoot member being configured to flex in response to application of a stride-related force, and to collectively exhibit at least two load-responsive phases of longitudinal flexion, said load-responsive phases including:

a first phase wherein a first force is applied to said foot structure, said midfoot member and said sub-arch section exhibiting counter-flexion wherein said midfoot member and said sub-arch section flex in opposite directions; and a second phase wherein a second force is applied to said foot structure, said second force being greater than said first force, said midfoot member and said sub-arch section exhibiting mutual flexion wherein said midfoot member and said sub-arch section flex together.

10. A lower extremity prosthetic device including a foot structure which comprises:

a heel member formed substantially from a first structural material of a first modulus of elasticity;

an elongate, dorsal midfoot member formed substantially from a second structural material having a second modulus of elasticity less than said first modulus of elasticity, said midfoot member extending arcuately forwardly from said heel member and including elongate medial and lateral arch elements, said arch elements being transversely spaced to accommodate torsional flexion of said midfoot member upon application of a stride-related force; and an elongate plantar member joined to and extending between said heel member and corresponding forward ends of said medial and lateral arch elements, said plantar member being formed substantially from a third structural material having a third modulus of elasticity less than said second modulus of elasticity.

11. The prosthetic device of claim 10, wherein said plantar member includes a toe section and a sub-arch section, said sub-arch section extending arcuately between said heel member and a forward end of said midfoot member, and said toe section extending forwardly from said sub-arch section.

12. The prosthetic device of claim 11, wherein said sub-arch section is laterally offset from a longitudinal center line of said foot structure.

13. The prosthetic device of claim 11, wherein said sub-arch section of said plantar member is positioned below said midfoot member, said sub-arch section and said midfoot member being configured to flex in response to application of a stride-related force, and to collectively exhibit at least two load-responsive phases of longitudinal flexion, said load-responsive phases including:

a first phase wherein a first force is applied to said foot structure, said midfoot member and said sub-arch section exhibiting counter-flexion wherein said midfoot member and said sub-arch section flex in opposite directions, and a second phase wherein a second force is applied to said foot structure, said second force being greater than said first force, said midfoot member and said sub-arch section exhibiting mutual flexion wherein said midfoot member and said sub-arch section flex together.

14. The prosthetic device of claim 10, wherein said foot structure further comprises a tongue-and-groove fastening arrangement for fastening said plantar member to said heel member, said fastening arrangement including a flared tongue which forms a part of said plantar member and a correspondingly-shaped groove defined in said heel member, said groove being configured to receive and hold said tongue.

* * * * *